(12) United States Patent
Spargo

(10) Patent No.: US 10,710,998 B2
(45) Date of Patent: Jul. 14, 2020

(54) COMPOUND AND PROCESS

(71) Applicant: VERONA PHARMA PLC, Cardiff (GB)

(72) Inventor: Peter Lionel Spargo, Harbledown (GB)

(73) Assignee: VERONA PHARMA PLC, Cardiff (GB)

( * ) Notice: Subject to any disclaimer, the term of this patent is extended or adjusted under 35 U.S.C. 154(b) by 0 days.

(21) Appl. No.: 16/309,435

(22) PCT Filed: Jul. 27, 2017

(86) PCT No.: PCT/GB2017/052190
§ 371 (c)(1),
(2) Date: Dec. 12, 2018

(87) PCT Pub. No.: WO2018/020249
PCT Pub. Date: Feb. 1, 2018

(65) Prior Publication Data
US 2019/0330206 A1    Oct. 31, 2019

(30) Foreign Application Priority Data

Jul. 28, 2016  (GB) .................................. 1613054.4

(51) Int. Cl.
*C07D 471/04*        (2006.01)
(52) U.S. Cl.
CPC .................................. *C07D 471/04* (2013.01)
(58) Field of Classification Search
CPC .................................................. C07D 471/04
See application file for complete search history.

(56) References Cited

U.S. PATENT DOCUMENTS

| | | | |
|---|---|---|---|
| 4,400,506 A | 8/1983 | Lal et al. |
| 4,482,556 A | 11/1984 | Lal et al. |
| 4,581,172 A | 4/1986 | Kaiser et al. |
| 6,794,391 B2 | 9/2004 | Oxford et al. |
| 7,105,663 B2 | 9/2006 | Oxford et al. |
| 7,378,424 B2 | 5/2008 | Oxford et al. |
| 8,242,127 B2 | 8/2012 | Oxford et al. |
| 9,062,047 B2 | 6/2015 | Walker et al. |
| 9,700,558 B2 | 7/2017 | Walker et al. |
| 9,717,732 B2 | 8/2017 | Walker et al. |
| 9,956,171 B2 | 5/2018 | Spargo et al. |
| 2003/0036542 A1 | 2/2003 | Oxford et al. |
| 2004/0171828 A1 | 9/2004 | Oxford et al. |
| 2004/0176353 A1 | 9/2004 | Oxford et al. |
| 2008/0206163 A1 | 8/2008 | Oxford et al. |
| 2012/0302533 A1 | 11/2012 | Oxford et al. |
| 2013/0225616 A1 | 8/2013 | Oxford et al. |
| 2016/0000790 A1 | 1/2016 | Walker et al. |
| 2016/0008363 A1 | 1/2016 | Walker et al. |
| 2017/0112839 A1 | 4/2017 | Abbott-Banner et al. |
| 2017/0239178 A1 | 8/2017 | Spargo et al. |
| 2017/0266190 A1 | 9/2017 | Walker et al. |
| 2018/0021337 A1 | 1/2018 | Spargo et al. |
| 2018/0369139 A1 | 12/2018 | Spargo et al. |

FOREIGN PATENT DOCUMENTS

| | | | |
|---|---|---|---|
| EP | 0075165 | 3/1983 | |
| GB | 1597717 | 9/1981 | |
| WO | 2000058308 | 10/2000 | |
| WO | WO 00/58308 | * 10/2000 | ........... C07D 471/04 |
| WO | 2016042313 | 3/2016 | |

OTHER PUBLICATIONS

Bansi et al. (1984) "Trequinsin, a potent new antihypertensive vasodilator in the series of 2-(arylimino)-3-alkyl-9,10-dimethoxy-3,4,6,7-tetrahydro-2H-pyrimido[6,1-a]isoquinolin-4-ones"; Journal of Medicinal Chemistry 27(11); pp. 1470-1480.

Kienzle et al, (1985) "Synthesis of 6,7-dihydro-2H-pyrimido[6,1-a]isoquinolin-4(3H)-ones and analogous compounds and their activity as blood platelet aggregation inhibitors"; Helvetica Chimica Acta 69(7); pp. 1671-1680 (with English translation).

* cited by examiner

*Primary Examiner* — Erich A Leeser
(74) *Attorney, Agent, or Firm* — Michael Rubin; Rudy J. Ng; Bozicevic, Field & Francis LLP

(57) ABSTRACT

The present invention relates to a novel nitrile derivative of a pyrimido[6,1-a]isoquinolin-4-one compound of formula (A). The invention further relates to a process for producing a compound of formula (A). The invention also relates to a process which comprises reducing a compound of formula (A). Compounds of the invention are useful in the production of compounds such as RPL554.

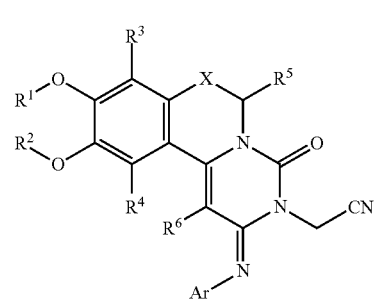

(A)

31 Claims, No Drawings

COMPOUND AND PROCESS

FIELD OF THE INVENTION

The invention relates to a novel nitrile derivate of a pyrimido[6,1-a]isoquinolin-4-one compound. The present invention further relates to a process for producing a nitrile derivative of a pyrimido[6,1-a]isoquinolin-4-one compound. The invention also relates to further processes useful in the production of pyrimido[6,1-a]isoquinolin-4-one compounds.

BACKGROUND OF THE INVENTION

RPL554 (9,10-dimethoxy-2-(2,4,6-trimethylphenylimino)-3-(N-carbamoyl-2-aminoethyl)-3,4,6,7-tetrahydro-2H-pyrimido[6,1-a]isoquinolin-4-one) is a dual PDE3/PDE4 inhibitor and is described in WO 00/58308, the entirety of which is incorporated by reference. As a combined PDE3/PDE4 inhibitor, RPL554 has both anti-inflammatory and bronchodilatory activity and is useful in the treatment of respiratory disorders such as asthma and chronic obstructive pulmonary disease (COPD). The structure of RPL554 is shown below.

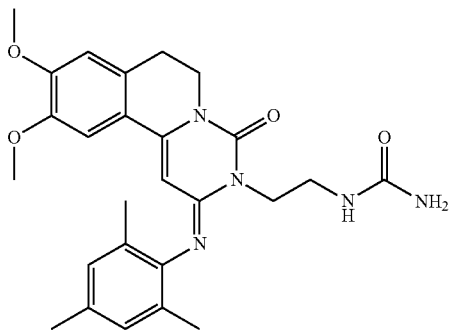 [SMILES: COc1cc2c(cc1OC)-c1c/c(=N\c3c(C)cc(C)cc3C)n(CCNC(N)=O)c(=O)n1CC2]

The known method for producing RPL554 uses phthalimidoethyl alkylation chemistry followed by deprotection using hydrazine (see WO 00/58308). However, yields of RPL554 achieved by this route are relatively low and not well suited to large scale production. There are also problems associated with the use of the genotoxic deprotecting agent hydrazine to remove the phthalimide group. Furthermore, phthalimidoethyl alkylation agents are relatively expensive.

There is therefore a need to develop a new route for the production of RPL554. In particular, it is desirable to develop a process with an improved yield. There is also a need to avoid the use of genotoxic compounds such as hydrazine. In addition, it would be useful to develop a method which is more atom-efficient and avoids the need to use expensive alkylating agents.

SUMMARY OF THE INVENTION

An improved method for producing pyrimido[6,1-a]isoquinolin-4-one compounds has been developed which proceeds via a novel nitrile intermediate. This new method has a favourable yield, is atom-efficient, and is readily scalable for the production of larger quantities of pyrimido[6,1-a]isoquinolin-4-one compounds.

The new process proceeds via a novel nitrile intermediate. The invention therefore further provides a nitrile compound or a salt thereof, which nitrile compound is a compound of formula (A):

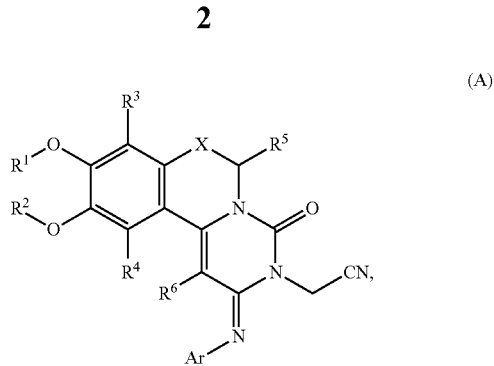

wherein:
$R^1$ and $R^2$ are the same or different and each is independently a $C_1$-$C_6$ alkyl group or a $C_2$-$C_7$ acyl group, or $R^1$ and $R^2$ together form a $C_1$-$C_6$ alkylene group;
$R^3$ and $R^4$ are the same or different and each is independently hydrogen, halogen or a $C_1$-$C_6$ alkyl group;
$R^5$ and $R^6$ are the same or different and each is independently hydrogen, halogen or a $C_1$-$C_6$ alkyl group;
X is $CHR^7$, O or $NR^7$, and $R^7$ is hydrogen or a $C_1$-$C_6$ alkyl group; and
Ar is a $C_6$-$C_{10}$ aryl group substituted with from 0 to 4 substituents, each of which substituents is independently halogen or a $C_1$-$C_6$ alkyl group.

The invention provides a process for producing a nitrile compound of formula (A):

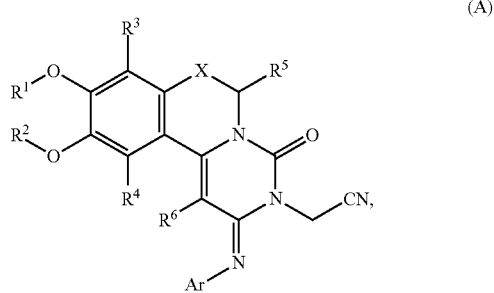

which process comprises reacting a compound of formula (I) with a compound of formula (II):

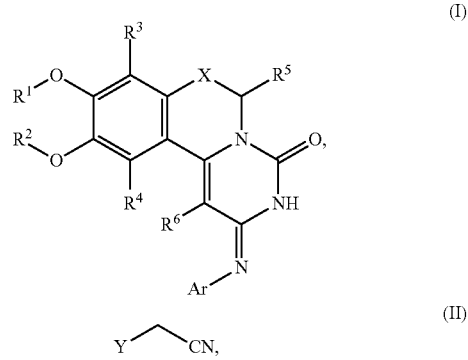

wherein:
$R^1$ and $R^2$ are the same or different and each is independently a $C_1$-$C_6$ alkyl group or a $C_2$-$C_7$ acyl group, or $R^1$ and $R^2$ together form a $C_1$-$C_6$ alkylene group;

R[3] and R[4] are the same or different and each is independently hydrogen, halogen or a $C_1$-$C_6$ alkyl group;

R[5] and R[6] are the same or different and each is independently hydrogen, halogen or a $C_1$-$C_6$ alkyl group;

X is CHR[7], O or NR[7], and R[7] is hydrogen or a $C_1$-$C_6$ alkyl group;

Ar is a $C_6$-$C_{10}$ aryl group substituted with from 0 to 4 substituents, each of which substituents is independently halogen or a $C_1$-$C_6$ alkyl group; and Y is a leaving group.

The nitrile compound of formula (A) can be readily converted to an amine compound which is an important intermediate in processes for producing pyrimido[6,1-a]isoquinolin-4-one compounds such as RPL554. The invention further provides a process for producing a compound of formula (B):

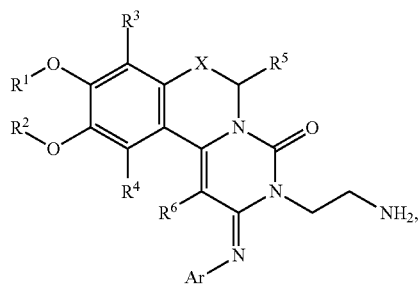

(B)

which process comprises reducing a compound of formula (A):

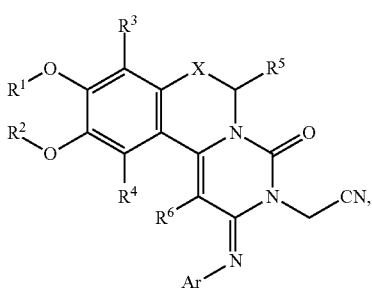

(A)

wherein each of R[1], R[2], R[3], R[4], R[5], R[6], X, Ar and Y is as defined herein.

As discussed above, the process of the invention allows the efficient and safe production of pyrimido[6,1-a]isoquinolin-4-one compounds such as RPL554. Further provided by the invention is a process for producing a compound of formula (C):

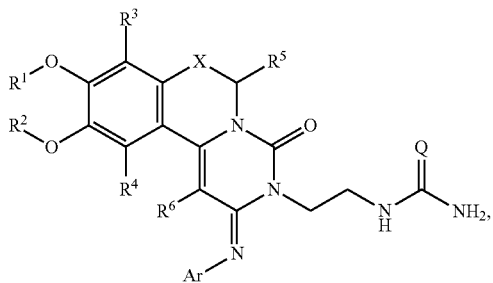

(C)

wherein each of R[1], R[2], R[3], R[4], R[5], R[6], X, Ar and Y is as defined herein, and Q is O, NR[8] or CR[8] and R[8] is hydrogen or a $C_1$-$C_6$ alkyl group wherein the process comprises:
(i) the preparation of a compound of formula (A) as defined herein; and/or
(ii) the reduction of a compound of formula (A) as defined herein.

The compound of formula (C) thereby obtained can be combined with a pharmaceutically acceptable carrier, excipient or diluent to obtain a pharmaceutical composition.

DETAILED DESCRIPTION OF THE INVENTION

As used herein, a $C_1$-$C_6$ alkyl group or moiety is a linear or branched alkyl group or moiety containing from 1 to 6 carbon atoms. Typically a $C_1$-$C_6$ alkyl group or moiety is a $C_1$-$C_4$ alkyl group or moiety. A $C_1$-$C_4$ alkyl group or moiety is a linear or branched alkyl group or moiety containing from 1 to 4 carbon atoms. Examples of $C_1$-$C_6$ alkyl groups and moieties include methyl, ethyl, n-propyl, i-propyl, n-butyl, i-butyl, t-butyl and 3-methyl-butyl. Examples of $C_1$-$C_4$ alkyl groups and moieties include methyl, ethyl, n-propyl, i-propyl, n-butyl, i-butyl and t-butyl. For the avoidance of doubt, where two alkyl moieties are present in a group, the alkyl moieties may be the same or different.

As used herein, a $C_1$-$C_6$ alkylene group or moiety is a linear or branched alkylene group or moiety. Examples include methylene, ethylene and n-propylene groups and moieties.

As used herein, halide is typically chlorine, fluorine, bromine or iodine.

As used herein, a $C_1$-$C_6$ alkoxy group is typically a said $C_1$-$C_6$ alkyl group attached to an oxygen atom.

As used herein, a $C_2$-$C_7$ acyl group is typically a said $C_1$-$C_6$ alkyl group attached to a —C(O)— group.

As used herein, a $C_6$-$C_{10}$ aryl group or moiety is typically phenyl or naphthyl. Phenyl is preferred.

Typically, in the process of the invention:
R[1] and R[2] are the same or different and each is methyl or ethyl;
R[3] and R[4] are the same or different and each is independently hydrogen or methyl;
R[5] and R[6] are the same or different and each is independently hydrogen or methyl;
X is CHR[7], and R[7] is hydrogen, methyl or ethyl;
Ar is a phenyl group substituted with from 0 to 4 substituents, each of which substituents is independently methyl or ethyl; and
Y is a leaving group.

Preferably, in the process of the invention:
$R^1$ and $R^2$ are methyl;
$R^3$ and $R^4$ are hydrogen;
$R^5$ and $R^6$ are hydrogen;
X is $CH_2$; and
Ar is 2,4,6-trimethylphenyl.

Thus, the compound of formula (I) is typically a compound of formula (Ia):

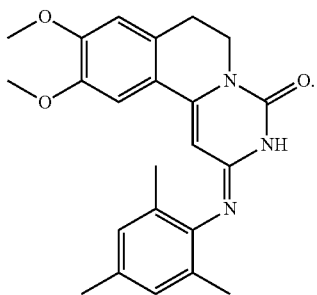

(Ia)

The compound of formula (I) may be obtained by known synthetic methods, for instance those described in WO 00/58308.

Leaving groups, for example the moiety Y in the formula (II), are well-known to the skilled person. Typically, a leaving group corresponds to the conjugate base of an acid having a $pK_a$ of less than 10.0, or less than 5.0, in water at 25° C. Examples of leaving groups include halides, perfluoroalkylsulfonates, arylsulfonates, alkylsulfonates, carboxylates, alkylthiolates, nitrates, phosphates and phosphate esters.

Y may, for instance, be selected from Cl, Br, I, —OC(O)$R^Y$, —OS(O)$_2R^Y$ and —S(O)$_2R^Y$, where $R^Y$ is hydrogen, a $C_1$-$C_6$ alkyl group, a $C_1$-$C_6$ alkoxy group or a $C_6$-$C_{10}$ aryl group, which alkyl, alkoxy or aryl group is optionally substituted with from 1 to 6 groups selected from nitrate and halide.

Typically, Y is a leaving group which is Br, I, mesylate ($CH_3SO_3^-$, OMs), tosylate ($CH_3C_6H_4SO_3^-$, OTs), nosylate ($O_2NC_6H_4SO_3^-$, ONs), acetate ($CH_3C(O)O^-$, OAc) or triflate ($CF_3SO_3^-$, OTf). Preferably, Y is a Br or I. For instance, the compound of formula (II) may be bromoacetonitrile or iodoacetonitrile. Most preferably, Y is Br.

In the reaction between the compounds of formulae (I) and (II), the amount of the compound of formula (II) is typically from 0.5 to 10.0 equivalents of the compound of formula (I). Preferably, the amount of the compound of formula (II) is from 1.0 to 2.5 equivalents of the compound of formula (I). For instance, the amount of compound (II) may be from 2.0 to 2.5 equivalents of the compound of formula (I).

Typically, the reaction between the compounds of formulae (I) and (II) comprises reacting the compound of formula (I) and the compound of formula (II) in the presence of a base. Suitable bases for catalysing such nucleophilic substitution reactions are well-known to the skilled person.

Typically, the base comprises carbonate, hydrogen carbonate, hydroxide, an alkoxide, a carboxylate or an amine. Examples of a base comprising carbonate include metal carbonates such as lithium carbonate, sodium carbonate, potassium carbonate, rubidium carbonate, caesium carbonate, magnesium carbonate, calcium carbonate, strontium carbonate and barium carbonate. Examples of a base comprising hydrogen carbonate include lithium hydrogen carbonate, sodium hydrogen carbonate, potassium hydrogen carbonate, rubidium hydrogen carbonate, caesium hydrogen carbonate, magnesium hydrogen carbonate, calcium hydrogen carbonate, strontium hydrogen carbonate and barium hydrogen carbonate.

Examples of a base comprising hydroxide include metal hydroxides of formula MOH and M(OH)$_2$, wherein M is a metal selected from lithium, sodium, potassium, rubidium, caesium, magnesium, calcium, strontium and barium. Examples of a base comprising an alkoxide include metal alkoxides of formula MOR and M(OR)$_2$, wherein M is a metal selected from lithium, sodium, potassium, rubidium, caesium, magnesium, calcium, strontium and barium and R is a $C_1$-$C_6$ alkyl group, for instance a MOEt, MO$^i$Pr and MO$^t$Bu. Examples of a base comprising a carboxylate include metal carboxylates of formula MOR or M(OR)$_2$, wherein M is a metal as defined herein and R is a $C_2$-$C_7$ acyl group, for instance MOAc or M(OAc)$_2$. Examples of a base comprising an amine include alkylamines of formula $NR_3$ wherein each R is independently H or a $C_1$-$C_6$ alkyl group.

Preferably, the base comprises carbonate, hydrogen carbonate or a carboxylate (for instance acetate). More preferably, the base is lithium carbonate, sodium carbonate, potassium carbonate, caesium carbonate, lithium acetate, sodium acetate or potassium acetate. Most preferably, the base is lithium carbonate or sodium acetate.

Typically, the base is used in an amount of from 1.0 to 10.0 equivalents of the compound of formula (I). Preferably, the amount of the base is from 1.5 to 4.0 equivalents of the compound of formula (I).

The process typically comprises reacting the compound of formula (I) and the compound of formula (II) in the presence of a solvent or mixtures of solvents. The solvent may be any suitable solvent, as are well-known to the skilled person. Examples of solvents include water and polar organic solvents. The solvent may be a protic polar solvent or an aprotic polar solvent. The organic solvent may be an alcohol (for instance methanol, ethanol, propanol or butanol), a ketone (for instance acetone or methylethylketone), a halogenated solvent (for instance chloroform, dichloromethane, chlorobenzene), an ether (for instance diethyl ether or tetrahydrofuran (THF)), an amide (for instance dimethyl formamide (DMF) or dimethyl acetamide (DMA)), and ester (for instance ethylacetate), a nitrile compound (for instance acetonitrile (ACN) or propionitrile) or a sulfoxide (for instance dimethyl sulfoxide).

Preferably, the solvent comprises a polar aprotic solvent. More preferably, the solvent comprises acetonitrile, tetrahydrofuran or dioxane. Most preferably, the solvent comprises acetonitrile.

Typically, the solvent comprises less than 10 vol % water, for instance less than 5.0 vol % or less than or equal to 1.0 vol % water.

The process typically comprises reacting the compound of formula (I) and the compound of formula (II) for at least 5 hours, preferably from 5 to 48 hours.

Typically, the process comprises reacting the compound of formula (I) and the compound of formula (II) at a temperature of from 50 to 100° C. For instance, the compounds may be reacted at a temperature of from 70 to 90° C.

Preferably, the process comprises reacting the compound of formula (I) and the compound of formula (II) in the presence of a solvent at reflux. The temperature required to attain reflux will depend on the solvent and is typically at or within 5° C. of the boiling point of that solvent at atmospheric pressure. The solvent may be as defined herein, for instance acetonitrile or THF.

In the process for producing the compound of formula (A), the compound of formula (II) may be bromoacetonitrile or iodoacetonitrile and the base may comprise carbonate (for instance lithium carbonate or sodium carbonate) or acetate (for instance sodium acetate or potassium acetate) and the compounds of formula (I) and (II) may be reacted in a polar aprotic solvent (for instance THF, dioxane or acetonitrile). A phase transfer catalyst may be used. In some cases, the solvent may comprise acetonitrile and the base may be lithium carbonate.

In an exemplary process according to the invention, the compound of formula (I), bromoacetonitrile, lithium carbonate and acetonitrile are combined in a vessel to form a reaction mixture. The reaction mixture may then be heated at reflux (for instance from 60 to 100° C.) for from 4 to 48 hours. The amount by weight of lithium carbonate is typically from 20 to 100 wt % relative to the weight of the compound of formula (I). The weight of acetonitrile may be from 10 to 100 times the weight of the compound of formula (I).

The compound of formula (A) may be recovered following the process for producing a compound of formula (A) by cooling the reaction mixture and filtering it, optionally at elevated temperature, followed by evaporation of the resulting solution to recover the compound of formula (A). In some cases, the process for producing the compound of formula (A) further comprises crystallising the compound of formula (A) from a solvent such as tetrahydrofuran.

Further provided by the invention is a process for producing a compound of formula (B) which process comprises reducing a compound of formula (A) as defined herein. Reducing the compound of formula (A) typically comprises reducing the nitrile group (—CN) in the compound of formula (A), typically to form a primary amine group (—$CH_2NH_2$) in place of the nitrile group.

Reducing a compound of formula (A) typically comprises: treating the compound of formula (A) with a reducing agent; or hydrogenating the compound of formula (A). Examples of reducing agents include hydrides (such as lithium aluminium hydride and lithium borohydride), boranes (such as diborane) and alkali metals (such as sodium or potassium, typically in an alcoholic solvent). Hydrogenating the compound of formula (A) typically comprises catalytic hydrogenation of the compound of formula (A), for instance by treating the compound of formula (A) with hydrogen gas in the presence of a metallic catalyst. Examples of metallic catalysts include catalysts comprising nickel, Raney nickel, palladium, palladium black, palladium hydroxide, platinum and platinum dioxide.

The metal catalyst is typically loaded with from 1 to 100 wt % of the metal, for instance from 10 to 100 wt %, from 20 to 100 wt % or from 50 to 100 wt %. The catalyst active weight is typically from 5 wt % to 100 wt %, for instance from 20 to 40 wt % or from 80 to 100 wt %.

Typically, reducing the compound of formula (A) comprises hydrogenating the compound of formula (A) in the presence of Raney nickel. Raney nickel is well-known to the skilled person and typically comprises a powdered alloy of nickel and aluminium. Raney nickel is commercially available. Typically, Raney nickel is used as a slurry in water.

Hydrogenating a compound of formula (A) is typically carried out in the presence of hydrogen gas under pressure and a metallic catalyst. The pressure of hydrogen may be from 1 bar to 50 bar, for instance from 2 bar to 20 bar. Typically, the pressure of hydrogen is from 5 to 15 bar, for example from 8 to 10 bar. Hydrogenation of the compound of formula (A) is typically carried out for at least 10 minutes or at least 1 hour, for instance from 1 to 24 hours.

Often, dissolved ammonia or gaseous ammonia is present during hydrogenation. Typically, the hydrogenation is carried out on a compound of formula (A) in a solvent which comprises dissolved ammonia. The ammonia is typically dissolved in a polar protic solvent, for instance water, methanol, ethanol or propanol. The concentration of ammonia in the solvent is typically from 1 to 20 M, for instance from 2 to 10 M. Preferably, the concentration of ammonia in the solvent (for instance methanol or methanol and water) is from 5 to 9 M.

Reducing the compound of formula (A) may for instance comprise hydrogenating the compound of formula (A) in the presence of Raney nickel and methanolic ammonia (optionally with an ammonia concentration of from 2 to 10 M) under hydrogen at a pressure of from 5 to 20 bar for at least 1 hour.

In some cases, the process for producing a compound of formula (B) as described herein further comprises, prior to reducing compound of formula (A), producing the compound of formula (A) by a process as defined herein.

The invention also provides a process for producing a compound of formula (C) as defined herein, which process comprises a process for producing a compound of formula (A) as defined herein or a process for producing a compound of formula (B) as defined herein. step (b) is an ureation reaction $R^1$, $R^2$, $R^3$, $R^4$, $R^5$, $R^6$, X, Ar, Y and Q in the compound of formula (C) may be as defined herein. Preferably: $R^1$ and $R^2$ are methyl; $R^3$ and $R^4$ are hydrogen; $R^5$ and $R^6$ are hydrogen; X is $CH_2$; Ar is 2,4,6-trimethylphenyl; and Q is O. Accordingly, the compound of formula (C) is preferably RPL554, the structure of which is shown above.

Typically, further reacting the compound of formula (B) to give a compound of formula (C) comprises performing a ureation reaction. A ureation reaction is a reaction that leads to the formation of a urea group, for instance by converting an amine group. A urea group is a group of formula —NHC(O)$NH_2$.

Typically, the process for producing a compound of formula (C) comprises reacting the compound of formula (B) with a compound of formula (III):

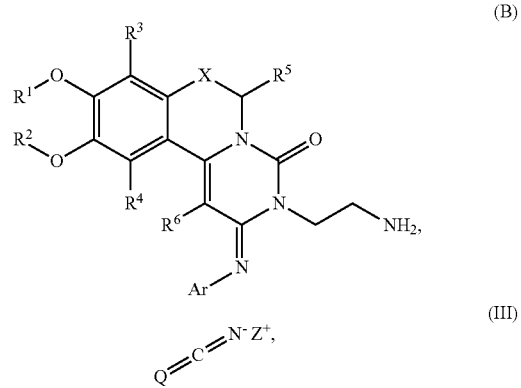

wherein $R^1$, $R^2$, $R^3$, $R^4$, $R^5$, $R^6$, X, Ar, Y and Q are as defined herein, and $Z^+$ is a metal cation, for instance sodium or potassium.

Typically, Q is O and the compound of formula (III) is a cyanate compound. For instance, the compound of formula (III) may be sodium cyanate. Processes for producing a compound of formula (C) from the compound of formula (B) are described in WO 00/58308.

Alternatively, a compound of formula (C) may be produced by reacting a compound of formula (B) with a compound comprising a chloroformate group, for instance 4-nitrophenyl chloroformate, and subsequent reaction with ammonia. For instance, the process for producing a compound of formula (C) may comprise reacting a compound of formula (B) with a compound of formula (IV)

(IV)

wherein $R^{IV}$ is an aryl group optionally substituted with one or more substituents selected from nitro groups and fluorine groups, and then reacting the product with ammonia.

The invention also provides a process for producing a pharmaceutical composition comprising (a) a compound of formula (C) and (b) a pharmaceutically acceptable carrier, diluent or excipient. Pharmaceutically acceptable carriers, diluents and excipients are known to the skilled person.

Preferably, the pharmaceutical composition is suitable for inhalation. More preferably, it is a dry powder, solution or suspension suitable for inhalation. Most preferably, it is a suspension as described in WO 2016/042313, the contents of which are incorporated herein by reference.

The invention also provides a nitrile compound or a salt thereof, which nitrile compound is a compound of formula (A).

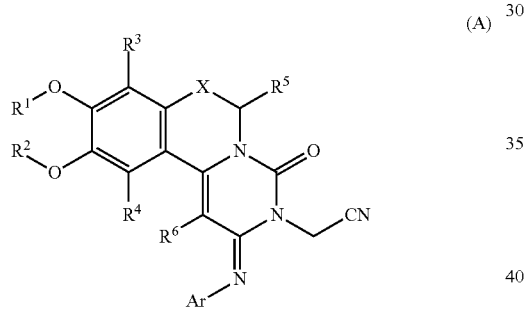

(A)

The compound of formula (A) may be as defined herein. For instance, in the compound of formula (A) the substituents may be defined as follows:

$R^1$ and $R^2$ are the same or different and each is methyl or ethyl;

$R^3$ and $R^4$ are the same or different and each is independently hydrogen or methyl;

$R^5$ and $R^6$ are the same or different and each is independently hydrogen or methyl;

X is $CHR^7$, and $R^7$ is hydrogen, methyl or ethyl; and

Ar is a phenyl group substituted with from 0 to 4 substituents, each of which substituents is independently methyl or ethyl.

Preferably, the nitrile compound is a compound of formula (D):

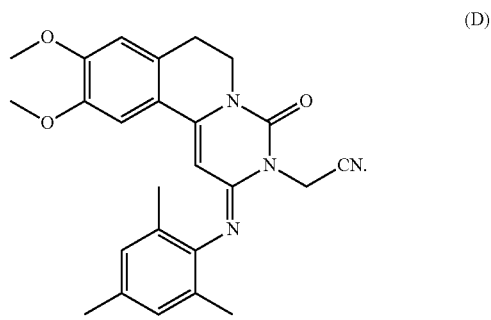 [SMILES: COc1cc2c(cc1OC)-c1c/c(=N\c3c(C)cc(C)cc3C)n(CC#N)c(=O)n1CC2]

(D)

The invention may be described in more detail by reference to the following examples.

EXAMPLES

The known phthalimidoethyl alkylation route was compared with the process of the invention proceeding via a nitrile intermediate. The two processes are summarised in the reaction scheme (Scheme 1) below.

Scheme 1

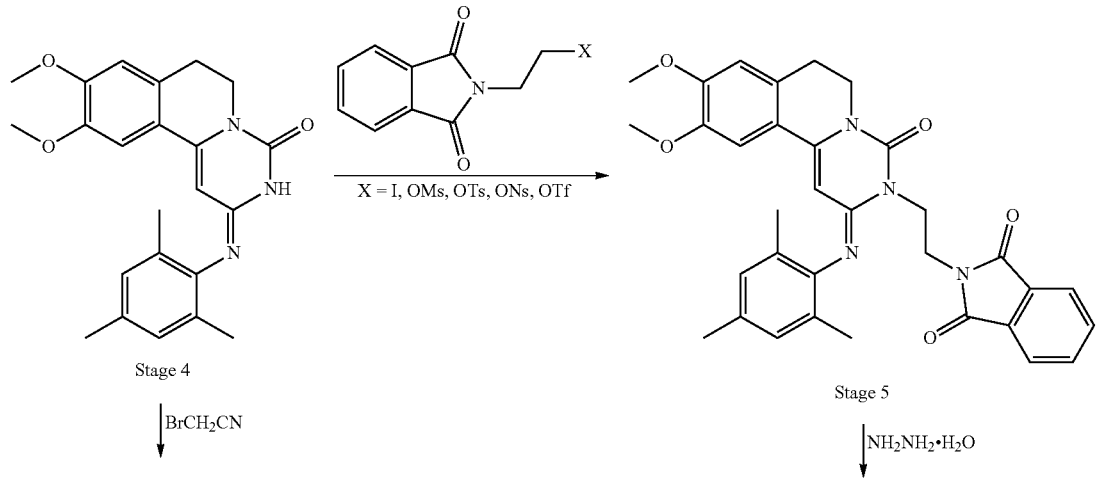

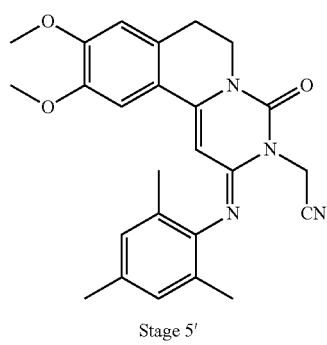

Stage 5'

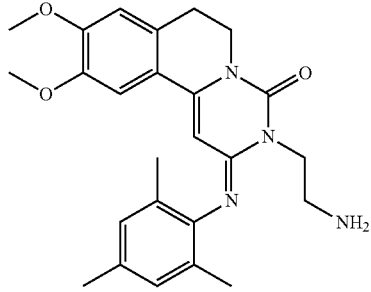

Stage 6

Comparative Example 1

Phthalimidoethyl Alkylation

Preparation of 9,10-dimethoxy-2-(2,4,6-trimethylphenylimino)-3-(2-N-phthalimidoethyl)-3,4,6,7-tetrahydro-2H-pyrimido[6,1-a]isoquinolin-4-one:

A mixture of 9,10-dimethoxy-2-(2,4,6-trimethylphenylimino)-3,4,6,7-tetrahydro-2H-pyrimido[6,1-a]isoquinolin-4-one (Stage 4 in Scheme 1, 60.0 g, 0.153 mol), potassium carbonate (191 g, 1.38 mol), sodium iodide (137 g, 0.92 mol) and N-(2-bromoethyl) phthalimide (234 g, 0.92 mol) in 2-butanone (1500 ml) was stirred and heated at reflux under nitrogen for 4 days. After cooling to room temperature the mixture was filtered and the filtrate was evaporated in vacuo. The residue was treated with methanol (1000 ml) and the solid filtered off, washed with methanol and recrystallised from ethyl acetate to obtain the Stage 5 compound of Scheme 1 as a pale yellow solid in yield 40.0 g, 46%. Evaporation of the mother liquor and column chromatography of the residue on silica gel (CH$_2$Cl$_2$/MeOH 95:5) provided further product 11.7 g, 13.5%.

Further work at a later stage identified that yields for the phthalimidoethyl alkylation step dropped to around 34% on average when performed on a multi-kilogram scale.

Example 1

Bromoacetonitrile Alkylation

An initial alkylation reaction using a large excess (8 equivalents) of bromoacetonitrile in the presence of sodium carbonate in cyclopentanone, gave complete consumption of the starting material (compound of formula (Ia), Stage 4 in Scheme 1), yielding two product regioisomers as indicated by LC, 72% and 12% respectively. The reaction conditions were altered to give a better reaction profile. The equivalents of bromoacetonitrile were reduced from 8 to 2.2, and the reaction was heated to 110° C. for 2 h. LC indicated two regioisomers of 87% and 8% which were later identified as the desired Stage 5' (N-alkylated) product (major isomer 87%) in Scheme 1 and the O-alkylated isomer (minor isomer 8%, shown below).

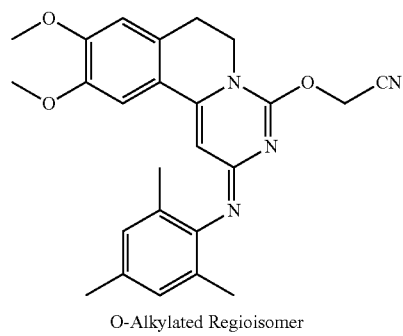

O-Alkylated Regioisomer

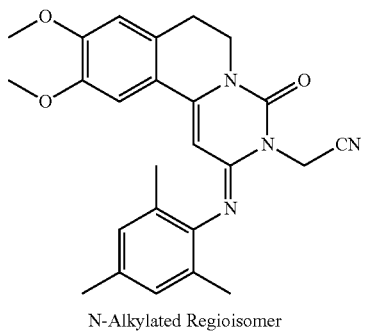

N-Alkylated Regioisomer

DMF was used to elute the product. A total of 6.5 g with a purity of 96% by LC was isolated (contained 3.5% of the O-alkylated isomer). Confirmation that this material was indeed the desired regiosiomer was obtained by reduction and comparison of the resulting product with an authentic sample of the amino product (Stage 6 in Scheme 1).

Example 2

A number of reactions using bromoacetonitrile were performed in order to improve the reaction profile. The first set of trial reactions involved the reaction of RPL554 Stage 4 with bromoacetonitrile in THF with various bases. THF was chosen over cyclopentanone (used previously) as it is considerably cheaper, could be used with strong bases and could be easily solvent swapped for methanol, which is used in the next stage. The results are shown in Table 1. "LC" stands for liquid chromatography.

TABLE 1

| Base (2.3 eq) | Alkylating agent (2.2 eq) | Temp/time | Solvent (30 vol) | Product % by LC | O-alkylated isomer % by LC | Stage 4 % LC |
|---|---|---|---|---|---|---|
| $Li_2CO_3$ | Bromoacetonitrile | 65/2 h | THF | 37 | 3 | 60 |
| $Na_2CO_3$ | Bromoacetonitrile | 65/2 h | THF | 21 | 4 | 72 |
| $K_2CO_3$ | Bromoacetonitrile | 65/2 h | THF | 19 | 29 | 51 |
| $Cs_2CO_3$ | Bromoacetonitrile | 65/2 h | THF | 13 | 31 | 45 |
| NaOAc | Bromoacetonitrile | 65/2 h | THF | 71 | 3.6 | 15 |
| KOAc | Bromoacetonitrile | 65/2 h | THF | 19 | 5.7 | 75 |
| NaO$^t$Bu | Bromoacetonitrile | 65/2 h | THF | 17 | 70 | 2 |
| KO$^t$Bu | Bromoacetonitrile | 65/2 h | THF | 9 | 80 | 3.5 |
| NaOEt | Bromoacetonitrile | 65/2 h | THF | 8 | 81 | 2 |

The bases that gave the most favourable results were lithium and sodium carbonate and sodium and potassium acetate. The strong bases generally favoured the formation of the unwanted O-alkylated isomer. The four most favourable reactions were allowed to stir overnight at 65° C. The results from these continued reactions are shown in Table 2.

TABLE 2

| Base (2.3 eq) | Alkylating agent (2.2 eq) | Temp/time | Solvent (30 vol) | Product % by LC | O-alkylated isomer % by LC | Stage4 % LC |
|---|---|---|---|---|---|---|
| $Li_2CO_3$ | Bromoacetonitrile | 65/16 h | THF | 91 | 3.6 | 5 |
| $Na_2CO_3$ | Bromoacetonitrile | 65/16 h | THF | 82 | 13 | <1 |
| NaOAc | Bromoacetonitrile | 65/16 h | THF | 90 | 3.7 | 1 |
| KOAc | Bromoacetonitrile | 65/16 h | THF | 85 | 6 | 5 |

As the results in Table 2 show, the two best sets of conditions were those using sodium acetate and lithium carbonate.

Example 3

The next set of reactions used those bases, sodium acetate and lithium carbonate, varying the amount of solvent and varying the number of equivalents of bromoacetonitrile to examine the possibility of a higher throughput reaction. The results are shown in Table 3.

TABLE 3

| Base (2.3 eq) | BrCH$_2$CN Equiv. | Temp/time | Solvent | Product % by LC | Other isomer % by LC | St4 % LC |
|---|---|---|---|---|---|---|
| $Li_2CO_3$ | 2.2 | 65/16 h | THF (20 vol) | 76 | 3.4 | 18 |
| $Li_2CO_3$ | 1.1 | 65/16 h | THF (20 vol) | 68 | 3 | 26 |
| $Li_2CO_3$ | 2.2 | 65/16 h | THF (10 vol) | 71 | 3 | 23 |
| $Li_2CO_3$ | 1.1 | 65/16 h | THF (10 vol) | 63 | 2.5 | 32.5 |
| NaOAc | 2.2 | 65/16 h | THF (20 vol) | 60 | 4.7 | 32 |
| NaOAc | 1.1 | 65/16 h | THF (20 vol) | 37 | 3.4 | 57 |
| NaOAc | 2.2 | 65/16 h | THF (10 vol) | 42 | 3.3 | 52 |
| NaOAc | 1.1 | 65/16 h | THF (10 vol) | 22 | 2 | 75 |

From Table 3 it can be seen that lowering the volumes of solvent can have a negative effect on the rate of reaction with sodium acetate as the base. This effect is not as great when lithium carbonate is used as the base. An increased number of equivalents of bromoacetonitrile (2.2 eq v 1.1 eq) also has a positive effect on the reaction. The reactions using lithium carbonate were allowed to stir for a further 24 h. The results are shown in Table 4. The reaction in THF is a slurry-to-slurry conversion; the slower reactions at apparently greater concentrations may be attributed to the fact that less Stage 4 starting material (SM) is actually in solution and available to react.

TABLE 4

| Base (2.3 eq) | BrCH$_2$CN Equiv. | Temp/time | Solvent | Product % by LC | O-alkylated isomer % by LC | Stage4 % LC |
|---|---|---|---|---|---|---|
| $Li_2CO_3$ | 2.2 | 65/40 h | THF (20 vol) | 91 | 4 | 4 |
| $Li_2CO_3$ | 1.1 | 65/40 h | THF (20 vol) | 87 | 4.2 | 8 |
| $Li_2CO_3$ | 2.2 | 65/40 h | THF (10 vol) | 92 | 3.5 | 4 |
| $Li_2CO_3$ | 1.1 | 65/40 h | THF (10 vol) | 90.5 | 2.85 | 6 |

All the reactions that were continued for a further 24 h went on to give similar completions to that observed with 30 vol of solvent, 2.2 eq of bromoacetonitrile with lithium carbonate after 16 h. This set of reactions demonstrates that very good results may be achieved using less bromoacetonitrile (1.1 eq v 2.2 eq) and less solvent (10 vol v 30 vol), provided that a longer stir out period can be accommodated.

Example 4

The next set of reactions looked at the use of iodoacetonitrile as the alkylating agent. The results are shown in Table 5.

TABLE 5

| Base (2.3 eq) | ICH$_2$CN Equiv. | Temp/ time | Solvent | Product % by LC | demethylated % by LC | Stage4 % LC |
|---|---|---|---|---|---|---|
| Li$_2$CO$_3$ | 2.2 | 65/16 h | THF | 53 | 5.2 | 30 |
| Li$_2$CO$_3$ | 1.1 | 65/16 h | THF | 33 | 1.7 | 55 |
| LiOAc | 1.12 | 65/16 h | THF | 34 | 5.5 | 50 |
| NaOAc | 1.1 | 65/16 h | THF | 31 | 11.7 | 47 |

Example 5

A further set of reactions looked at lithium carbonate (the most effective base observed in previous experiments) in 2-MeTHF (a higher boiling solvent to facilitate achievement of higher reaction temperature and thus in principle quicker reactions) with variable amounts of bromoacetonitrile and solvent. The results are shown in Table 6.

TABLE 6

| Base (2.3 eq) | BrCH$_2$CN Equiv. | Temp/ time | Solvent | Product % by LC | O-alkylated isomer % by LC | Stage4 % LC |
|---|---|---|---|---|---|---|
| Li$_2$CO$_3$ | 2.2 | 80/16 h | 2MeTHF (30 vol) | 48 | 2 | 46 |
| Li$_2$CO$_3$ | 2.2 | 80/16 h | 2MeTHF (20 vol) | 30 | 1.6 | 65 |
| Li$_2$CO$_3$ | 1.1 | 80/16 h | 2MeTHF (20 vol) | 37 | 1.6 | 57 |
| Li$_2$CO$_3$ | 2.2 | 80/16 h | 2MeTHF (10 vol) | 20 | 1.1 | 76 |
| Li$_2$CO$_3$ | 1.1 | 80/16 h | 2MeTHF (10 vol) | 20 | 1.1 | 76 |

These results suggest that the solubility of the starting material in 2-MeTHF is not as good as in THF and hence the conversion to product is slower despite the higher reaction temperature.

Example 6

Returning to bromoacetonitrile as alkylating agent, two small scale reactions were performed used lithium carbonate and lithium acetate in 5% water:THF as the solvent. The reaction using lithium acetate was less favourable in terms of conversion to product and the reaction using lithium carbonate gave higher than expected levels of the unwanted O-alkylated isomer. These reactions also suggest that water may have a negative effect on the reaction. The results are shown in Table 7.

TABLE 7

| Base (2.3 eq) | Alkylating agent | Temp/ time | Solvent | Product % by LC | O-alkylated isomer % by LC | Stage4 % LC |
|---|---|---|---|---|---|---|
| Li$_2$CO$_3$ | BrCH$_2$CN 1.1 eq | 65/16 h | 5% water:THF (10 vol) | 65 | 9.5 | 21.5 |
| LiOAc | BrCH$_2$CN 1.1 eq | 65/16 h | 5% water:THF (10 vol) | 19 | 3 | 76 |

Example 7

Two 10 g alkylation reactions were performed in THF using lithium acetate and lithium carbonate respectively as the base. The reactions were slower than expected based on previous experiments (e.g. Table 9). The conversions after 16 h are shown in Table 8. It was postulated that a grinding effect of the stirrer bar in the previous smaller scale reactions may have accelerated the reaction by making smaller particles of the inorganic base and thus increasing the available surface area for reaction.

TABLE 8

| Base (2.3 eq) | BrCH$_2$CN Equiv. | Temp/ time | Solvent | Product % by LC | O-alkylated isomer % by LC | Stage4 % LC |
|---|---|---|---|---|---|---|
| LiOAc | 1.1 | 65/16 h | THF (10 vol) | 11.5 | <1 | 85 |
| Li$_2$CO$_3$ | 1.1 | 65/16 h | THF (10 vol) | 22 | <1 | 74 |

Further THF (10 vol) and bromoacetonitrile (1.1 eq.) were added to the reactions in a bid to increase the reaction rate. The results after 48 h are shown in Table 9.

TABLE 9

| Base (2.3 eq) | BrCH$_2$CN Equiv. | Temp/ time | Solvent | Product % by LC | O-alkylated isomer % by LC | Stage4 % LC |
|---|---|---|---|---|---|---|
| LiOAc | 2.2 | 65/48 h | THF (20 vol) | 14.4 | <1 | 82 |
| Li$_2$CO$_3$ | 2.2 | 65/48 h | THF (20 vol) | 69 | 3 | 24 |

The lithium carbonate reaction was continued for a further 24 h to give 85% product, 7% starting material, 3.1% of the unwanted O-alkylated isomer and a previously unseen impurity of 2.7% (LCMS showed a mass of MH$^+$ of 470, suggestive of bis-alkylation—see below). The reaction supernatant was enriched with impurities and contained very little product as seen by LC, suggesting that the desired product may have crystallised out. The solid was isolated via filtration; analysis indicated 90.5% desired product, 6% starting material, <1% of the unwanted O-alkylated regioisomer and <1% of the other major impurity (RT 14.5).

Example 8

The use of more polar solvents was investigated. Two 10 g reactions were performed using lithium carbonate in acetonitrile and in dioxane. These reactions were quicker, although it should be noted that the stage 4 starting material and the lithium carbonate were both ground up prior to use in these reactions. The results are shown in Table 10.

TABLE 10

| Base (2.3 eq) | BrCH$_2$CN Equiv. | Temp/ time | Solvent | Product % by LC | O-alkylated isomer % by LC | Stage4 % LC | Unknown impurity |
|---|---|---|---|---|---|---|---|
| Li$_2$CO$_3$ | 2.2 | 82/16 h | Acetonitrile (20 vol) | 94 | <0.5 | 0 | 4.2 |
| Li$_2$CO$_3$ | 2.2 | 100/16 h | Dioxane (20 vol) | 83 | 4.7 | 4.3 | 7.3 |

The reactions were concentrated to near dryness and the diluted with THF (20 vol) and slurried for 30 mins before filtering. The analysis of the solid isolated is shown in Table 11.

TABLE 11

| Base (2.3 eq) | BrCH$_2$CN Equiv. | Temp/time | Solvent | Product % by LC | O-alkylated isomer % by LC | Stage4 % LC | Unknown impurity |
|---|---|---|---|---|---|---|---|
| Li$_2$CO$_3$ | 2.2 | 82/16 h | Acetonitrile (20 vol) | 95.5 | 0 | 0 | 2.5 |
| Li$_2$CO$_3$ | 2.2 | 100/16 h | Dioxane (20 vol) | 91 | 0 | 1 | 6 |

Example 9

The three 10 g bromoacetonitrile alkylation reactions using THF, acetonitrile and dioxane with lithium carbonate as the base were combined post THF slurries. The organic residue was dissolved in dichloromethane:methanol (500 mL:50 mL) and the mixture filtered to remove insoluble materials (mainly lithium carbonate). The organics were concentrated to near dryness before slurrying in THF (400 mL).

The solid was filtered and dried to give 30 g active product (91% yield based on Stage 4 starting material). LC indicated a purity of 97.5% with a single impurity of 2.5%, which was believed to be a dialkylated species.

Example 10

Three further 10 g bromoacetonitrile alkylation reactions in acetonitrile were performed with lithium carbonate, sodium carbonate and potassium carbonate as the bases. It should be noted that in this set of reactions, neither the Stage 4 starting material nor the base was ground up prior to use. The results are shown in Table 12.

TABLE 12

| Base (2.3 eq) | BrCH$_2$CN Equiv. | Temp/time | Solvent | Product % by LC | O-alkylated isomer % by LC | Stage4 % LC |
|---|---|---|---|---|---|---|
| Li$_2$CO$_3$ | 2.2 | 82/18 h | Acetonitrile (20 vol) | 90 | 0 | 4.7 |
| Na$_2$CO$_3$ | 2.2 | 82/18 h | Acetonitrile (20 vol) | 56 | 11 | 18.6 |
| K$_2$CO$_3$ | 2.2 | 82/18 h | Acetonitrile (20 vol) | 8 | 2.6 | 82 |

It can clearly be seen from Table 12 that lithium carbonate gave the best results.

Example 11

A large scale reaction was conducted using acetonitrile as the solvent and lithium carbonate as the base.

A 10 g alkylation reaction in acetonitrile with lithium carbonate was performed whereby the amount of bromoacetonitrile was reduced from 2.2 eq. to 1.1 eq, LC after 18 h indicated 75% product, 19% starting material and 2% dialkylated. The reaction was continued for a further 24 h. LC analysis indicated 90% product and 7% starting material and 2.7% dialkylated. The reaction was cooled to room temperature and filtered to remove mostly lithium carbonate (the solid contained only a small amount of entrained product). The filtrate was concentrated in vacuo and THF (200 mL) was added to the residue. The resulting slurry was heated to reflux for 20 mins and the solid filtered off and dried in the oven overnight. LC analysis of the dried material indicated 98.2% purity. A total of 11.8 g was obtained (11.02 g=100% yield.). $^1$H NMR assay (using an internal standard) indicated an activity of 77%. The sample contained 9% THF and thus the NMR assay suggests that the solid contains approximately 14% w/w of inorganics (lithium salts). The active yield for the reaction was calculated to be 83%.

Example 12

A 100 g scale alkylation reaction was performed using 2.2 eq. of the bromoacetonitrile (higher level to reduce the overall reaction time). The reaction was stirred overnight in acetonitrile at reflux. LC completion after this time indicated 91% product and 4% starting material. The reaction was cooled to room temperature and filtered to remove the base. The filtrate was concentrated and the residue slurried in hot THF and filtered; the product was dried to give 123 g of product which had an assay of 77% by NMR, suggesting the entrainment of inorganic material. NMR assay of the resulting material indicated an activity of >95%, which was confirmed by HPLC analysis using the RPL554 stage 5 LC method, which indicated a purity of 96% with no single impurity >0.7%.

Example 13

An aliquot of the 77% purity solid from Example 11 was treated with water and the pH measured at pH 3-4, which was perhaps indicative of trace acid (HBr). Further processing was therefore performed to remove inorganics. The larger scale batch from Example 12 (Li$_2$CO$_3$/MeCN) was dissolved in dichloromethane (20 vol) and washed with 10% potassium carbonate solution (20 vol). The organics were then dried, filtered and concentrated in vacuo. The material was assayed by NMR at this point and this indicated a purity of >95%. A sample of this material was analysed the RPL554 stage 5 LC method indicated a purity of 94% with the only one impurity greater than 1%, which was the stage 4 starting material (3.4%), i.e. the compound of formula (Ia). A total of 95 g (green solid) was obtained for this reaction (86% yield).

Example 14

High Yield Process

To a 2 L jacketed vessel was added the RPL554 stage 4 (100 g), acetonitrile (2000 mL), lithium carbonate (43.4 g) and bromoacetonitrile (39.2 mL). The reaction was heated to 81° C. (reflux) overnight. LC analysis indicated 91% product and 4% starting material. The reaction was cooled to room temperature and filtered to remove lithium carbonate. The filtrate was concentrated in vacuo. The residue was slurried in THF (2 L) for 3 h at rt. The solid was filtered to give 123 g, $^1$H NMR assay indicated an activity of 77%. The solid was dissolved in dichloromethane (2.4 L) and washed with 10% potassium carbonate (2.4 L). The organics were separated, dried, filtered and concentrated. A total of 95 g was obtained as a green solid (86%). LC analysis indicated 93.9% product and 3.4% starting material.

Example 15

Reduction of Nitrile Intermediate Compound

A portion of the material from a successful bromoacetonitrile alkylation reaction was subjected to an atmospheric hydrogenation using Raney Ni and 7N methanolic ammonia (i.e. to produce Stage 6 in Scheme 1). THF was later added to improve solubility. The reaction was analysed via LC after 2 h and this indicated the formation of a compound with a similar retention time to the known Stage 6 compound 3-(2-aminoethyl)-2-(mesitylimino)-9,10-dimethoxy-2,3,6,7-tetrahydro-4H-pyrimido[6,1-a]isoquinolin-4-one (9.589 mins v 9.657 mins). The reaction was stirred under an atmosphere of hydrogen overnight. It was observed that a lot of the solvent had evaporated overnight, so further THF and 7N methanolic ammonia were added. LC analysis indicated 8% of the Stage 6 product. The mixture was pressurised to 5 bar and stirred for 3 h, LC indicated 42% of the Stage 6 compound with two impurities of 8%. The reaction was continued overnight, however LC showed no further change.

Example 16

The reaction in Example 15 was repeated using 50 vol of 7N methanolic ammonia (20 vol used before) and an increased amount of Raney Ni (100 wt % versus 14 wt %). The reaction was allowed to stir overnight under 9 bar of hydrogen, LC indicated 92.6% of the product. A sample was taken and analysed by $^1$H NMR. This showed a profile similar to the desired Stage 6 amine. The reaction was treated to an acidic work up. The product was precipitated using NaHCO$_3$ and filtered. A portion of the solid was dried and analysed via $^1$H NMR and was consistent with the Stage 6 product.

Example 17

A portion of the product obtained from Example 16 was further reacted to form RPL554, i.e. reaction with 4-nitrophenyl chloroformate followed by ammonia to give RPL554. LC indicated a purity of 97% with a largest single impurity of 1.5%. $^1$H NMR, $^{13}$C NMR and LC retention time were identical those for RPL554 produced previously, thus proving that this route can be used to successfully synthesise RPL554.

Example 18

The use of a mixture of aqueous ammonia and methanol was also investigated as an alternative to methanolic ammonia. The results are shown in Table 13.

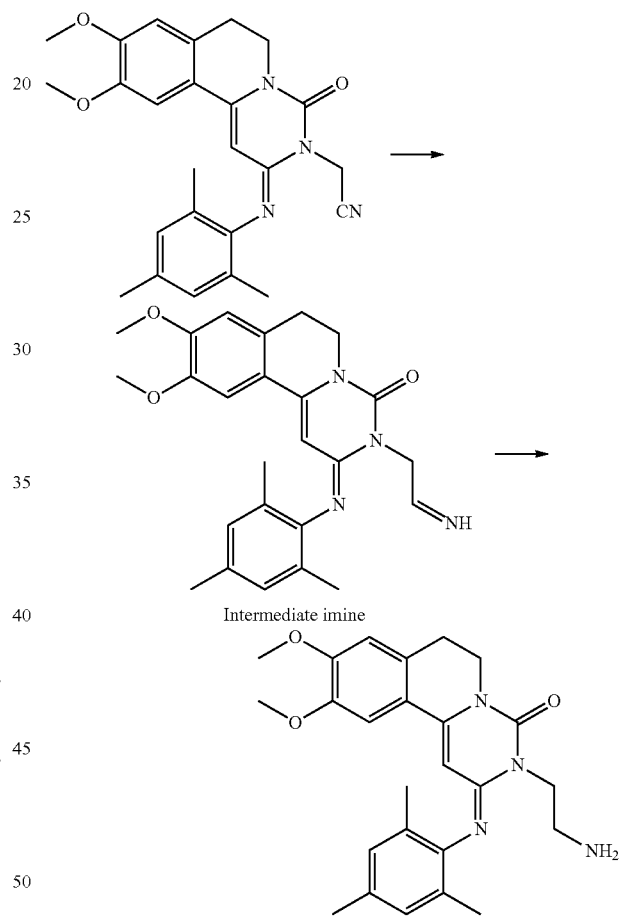

Intermediate imine

TABLE 13

| Catalyst Active wt % | Time/ Temp | Pressure | Solvent | Product % by LC | Intermediate imine % by LC | SM % LC |
|---|---|---|---|---|---|---|
| 7 wt % | 72 h/rt | 9 bar | 7N NH$_3$ MeOH (50 vol) | 9 | 16 | 64 |
| 28 wt % | 72 h/rt | 9 bar | 7N NH$_3$ MeOH (50 vol) | 55 | 19 | 18 |
| 7 wt % | 72 h/rt | 9 bar | 4:1 MeOH:NH$_{3(aq)}$ (50 vol) | 10 | 41 | 31 |
| 28 wt % | 72 h/rt | 9 bar | 4:1 MeOH:NH$_{3(aq)}$ (50 vol) | 51 | 13 | 4 |

These results indicate that the methanolic ammonia and the aqueous ammonia:methanol mixture both gave similar conversions to product. However, the LC profiles of the methanolic ammonia reactions were cleaner, with less side products observed. The second reaction in the table was scaled up to 1 g, using overhead stirring for 18 h. The LC completion after 18 h is shown in Table 14.

TABLE 14

| Catalyst Active wt % | Time/ Temp | Pressure | Solvent | Product % by LC | Intermediate imine % by LC | SM % LC |
|---|---|---|---|---|---|---|
| 28 wt % | 18 h/rt | 9 bar | 7N NH$_3$ MeOH (50 vol) | 48 | 17 | 30 |
| 28 wt % | Further 24 h/60° C. | 9 bar | 7N NH$_3$ MeOH (50 vol) | 92.6 | 2.3 | 0 |

The LC completion was similar to that of the smaller scale reaction, despite the more effective stirring. It was therefore decided to heat the reaction to 60° C. overnight under 9 bar of hydrogen. This effected complete reaction; the result is also summarised in Table 14. The catalyst was filtered off and the organics concentrated. The residue was dissolved in 1 M HCl and washed with dichloromethane (×3). The aqueous phase was then basified with sodium hydrogen carbonate to precipitate the product. The solid was filtered and dried under vacuum at 50° C. to give 655 mg of product amine (65% yield). LC indicated a purity of 97.5% with no single impurity >1%. The modest recovery may be attributed to the dichloromethane washes which were shown by LC to contain some product.

Example 19

A number of small scale reduction reactions were performed whereby the amount of solvent was varied along with varying the molarity of the methanolic ammonia. The reactions were heated to 60° C. under 9 bar of hydrogen for 18 h. The results are shown in Table 15.

TABLE 15

| Catalyst Active wt % | Time/ Temp | Pressure | Solvent | Product % by LC | Imine % by LC | SM % LC |
|---|---|---|---|---|---|---|
| 31 wt % | 18 h/60° C. | 9 bar | 7N NH$_3$ MeOH (50 vol) | 56 | 10 | 8.5 |
| 31 wt % | 18 h/60° C. | 9 bar | 7N NH$_3$ MeOH (40 vol) | 46 | 11.8 | 8 |
| 31 wt % | 18 h/60° C. | 9 bar | 7N NH$_3$ MeOH (30 vol) | 25 | 18 | 10 |
| 31 wt % | 18 h/60° C. | 9 bar | 7N NH$_3$ MeOH (20 vol) | 25 | 16 | 14 |
| 31 wt % | 18 h/60° C. | 9 bar | 3.5N NH$_3$ MeOH (50 vol) | 70 | 4 | 5 |
| 31 wt % | 18 h/60° C. | 9 bar | 1N NH$_3$ MeOH (50 vol) | 72 | 3 | 6 |

Further reactions were performed by first stirring at ambient temperature under 9 bar of hydrogen for 18 h, then stirring at 60° C. under 9 bar of hydrogen for 18 h. Table 16 shows the results after 18 h at room temperature (rt). Table 17 shows the reaction results after subsequently heating with pressure for a further 24 h.

TABLE 16

| Catalyst Active wt % | Time/ Temp | Pressure | Solvent | Product % by LC | Imine % by LC | SM % LC |
|---|---|---|---|---|---|---|
| 33 wt % | 18 h/rt | 9 bar | 7N NH$_3$ MeOH (50 vol) | 47 | 23 | 21 |
| 33 wt % | 18 h/rt | 9 bar | 7N NH$_3$ MeOH (40 vol) | 11 | 12 | 71 |
| 33 wt % | 18 h/rt | 9 bar | 7N NH$_3$ MeOH (30 vol) | 27.5 | 17.4 | 48.6 |
| 33 wt % | 18 h/rt | 9 bar | 7N NH$_3$ MeOH (20 vol) | 27.4 | 16.1 | 52.7 |
| 33 wt % | 18 h/rt | 9 bar | 3.5N NH$_3$ MeOH (50 vol) | 19.6 | 17.1 | 59 |

TABLE 16-continued

| Catalyst Active wt % | Time/Temp | Pressure | Solvent | Product % by LC | Imine % by LC | SM % LC |
|---|---|---|---|---|---|---|
| 33 wt % | 18 h/rt | 9 bar | 1N NH$_3$ MeOH (50 vol) | 33 | 17.9 | 41.7 |

TABLE 17

| Catalyst Active wt % | Time/Temp | Pressure | Solvent | Product % by LC | Imine % by LC | SM % LC |
|---|---|---|---|---|---|---|
| 33 wt % | 24 h/60° C. | 9 bar | 7N NH$_3$ MeOH (50 vol) | 85 | 8 | 1 |
| 33 wt % | 24 h/60° C. | 9 bar | 7N NH$_3$ MeOH (40 vol) | 37 | 25 | 7 |
| 33 wt % | 24 h/60° C. | 9 bar | 7N NH$_3$ MeOH (30 vol) | 47.7 | 28 | 1 |
| 33 wt % | 24 h/60° C. | 9 bar | 7N NH$_3$ MeOH (20 vol) | 45 | 21 | <1 |
| 33 wt % | 24 h/60° C. | 9 bar | 3.5N NH$_3$ MeOH (50 vol) | 56.6 | 16.5 | 2.4 |
| 33 wt % | 24 h/60° C. | 9 bar | 1N NH$_3$ MeOH (50 vol) | 85.4 | 6.7 | 1 |

It can be seen that the best two reactions are using 50 vol of methanol (1N and 7N, results 1 and 6 from Table 17) and within experimental error this result is essentially similar to that of the 1 g reaction performed previously using an overhead stirrer (Table 14).

Example 20

Experiments were conducted to investigate whether other solvents might facilitate the reaction by conferring greater solubility on the starting material, and perhaps allowing lower solvent volumes to be used. A number of small scale (60 mg) nitrile reductions were therefore performed in a mixture of 2N methanolic ammonia with THF, DMF and DMA. The results of these reactions are shown in Table 18.

TABLE 18

| Catalyst Active wt % | Time/Temp | Pressure | Solvent | Product % by LC | Imine % by LC | SM % LC |
|---|---|---|---|---|---|---|
| 33 wt % | 48 h/rt then 24 h at 60° C. | 9 bar | 2N NH$_3$ MeOH:THF (20:20 vol) | 4 | 7 | 70 |
| 33 wt % | 48 h/rt then 24 h at 60° C. | 9 bar | 2N NH$_3$ MeOH:DMF (20:20 vol) | 41 | 0.5 | 48 |
| 33 wt % | 48 h/rt then 24 h at 60° C. | 9 bar | 2N NH$_3$ MeOH:DMA (20:20 vol) | 55 | 0.5 | 31.5 |
| 33 wt % | 48 h/rt then 24 h at 60° C. | 9 bar | 2N NH$_3$ MeOH:THF (10:10 vol) | 21 | 5 | 50.4 |
| 33 wt % | 48 h/rt then 24 h at 60° C. | 9 bar | 2N NH$_3$ MeOH:DMF (10:10 vol) | 36 | 1 | 52 |
| 28 wt % | 48 h/rt then 24 h at 60° C. | 9 bar | 2N NH$_3$ MeOH:DMA (10:10 vol) | 33 | 0.5 | 53 |

Example 21

Reactions similar to those detailed in Example 20 were conducted using the purified stage 5' compound (2-(2-(mesitylimino)-9,10-dimethoxy-4-oxo-6,7-dihydro-2H-pyrimido[6,1-a]isoquinolin-3(4H)-yl)acetonitrile) for subsequent investigations. The number of volumes of solvent were reduced. Results using this input material are shown in Table 19.

TABLE 19

| Catalyst Active wt % | Time/ Temp | Pressure | Solvent | Product % by LC | Imine % by LC | SM % LC | Dimer % by LC |
|---|---|---|---|---|---|---|---|
| 33 wt % | 18 h/rt | 9 bar | 7N NH₃ MeOH (30 vol) | 33 | 8 | 44.7 | 2 |
| 33 wt % | 18 h/rt | 9 bar | 7N NH₃ MeOH (20 vol) | 54 | 8 | 21 | 5 |
| 33 wt % | 18 h/rt | 9 bar | 7N NH₃ MeOH:DMF (15 vol:15 vol) | 48 | 4 | 38 | 4 |
| 33 wt % | 18 h/rt | 9 bar | 7N NH₃ MeOH:DMA (15 vol:15 vol) | 38 | 3.3 | 47 | 3.3 |
| 33 wt % | 18 h/rt | 9 bar | 7N NH₃ MeOH:DMF (10 vol:10 vol) | 13 | 4.8 | 75 | <1 |
| 33 wt % | 18 h/rt | 9 bar | 7N NH₃ MeOH:DMA (10 vol:10 vol) | 12 | 5.3 | 75 | 1 |

The first four reactions in the table gave some conversion to product and imine intermediate, but were incomplete.

Example 22

The reactions in Example 21 were repeated except that they were conducted at 60° C. under 9 bar of hydrogen. The results are shown in Table 20. It can clearly be seen that as the temperature is elevated in these reactions the amount of dimerization increases significantly.

TABLE 20

| Catalyst Active wt % | Time/ Temp | Pressure | Solvent | Product % by LC | imine % by LC | SM % LC | Dimer % by LC |
|---|---|---|---|---|---|---|---|
| 33 wt % | 18 h/60° C. | 9 bar | 7N NH₃ MeOH (30 vol) | 37 | 19 | 2 | 32 |
| 33 wt % | 18 h/60° C. | 9 bar | 7N NH₃ MeOH (20 vol) | 52 | 11 | 1 | 26 |
| 33 wt % | 18 h/60° C. | 9 bar | 7N NH₃ MeOH:DMF (15 vol:15 vol) | 37 | 5 | 9 | 33 |
| 33 wt % | 18 h/60° C. | 9 bar | 7N NH₃ MeOH:DMA (15 vol:15 vol) | 37 | 2 | 16 | 32 |
| 33 wt % | 18 h/60° C. | 9 bar | 7N NH₃ MeOH:DMF (10 vol:10 vol) | 6 | 10 | 40 | 21 |
| 33 wt % | 18 h/60° C. | 9 bar | 7N NH₃ MeOH:DMA (10 vol:10 vol) | 9 | 7 | 40 | 21 |

Example 23

To mitigate dimer formation, the processes of Example 22 were repeated at higher dilution. A 1 g Raney nickel reaction was performed on purified 2-(2-(mesitylimino)-9,10-dimethoxy-4-oxo-6,7-dihydro-2H-pyrimido[6,1-a]isoquinolin-3(4H)-yl)acetonitrile (stage 5') using 50 wt % catalyst in 50 volumes of 7N MeOH:NH₃. The reaction was stirred for 2 days under 9 bar of hydrogen, LC indicated 71% product, 3.9% imine, 11.6% starting material.

Example 24

The effect of three parameters on hydrogenation on an intermediate scale were investigated: amount of solvent (30 volumes or 50 volumes); molarity of methanolic ammonia (1N versus 7N); and the amount of Raney Nickel catalyst (50 wt %, 75 wt % of 100 wt %). After the first two reactions using 30 and 50 volumes respectively with 50 wt % active catalyst it became clear that 50 volumes of solvent was better than 30 volumes.

TABLE 21

| Catalyst Active wt % | Time/ Temp | Pressure | Solvent | Product % by LC | Imine % by LC | SM % LC | Dimer % LC |
|---|---|---|---|---|---|---|---|
| 50 wt % | 72 h/rt | 9 bar | 7N NH₃ MeOH (30 vol) | 56 | 7 | 29 | 2 |
| 50 wt % | 48 h/rt | 9 bar | 7N NH₃ MeOH (50 vol) | 71 | 4 | 11 | trace |

The second set of reactions used 100 wt % active catalyst with 50 volumes of 1N and 7N methanolic ammonia. A reaction with 50 volumes of 7N methanolic ammonia was subsequently performed with active temperature maintenance at 20° C. overnight using an oil bath. The reaction went to completion (91.7% product) overnight. The details are shown in Table 22.

TABLE 22

| Catalyst Active wt % | Time/ Temp | Pressure | Solvent | Product % by LC | Imine % by LC | SM % LC | Dimer % by LC |
|---|---|---|---|---|---|---|---|
| 100 wt % | 48 h/rt | 9 bar | 1N NH$_3$ MeOH (50 vol) | 82.5 | 3.4 | 2.7 | 3.5 |
| 100 wt % | 18 h/ 20° C. | 9 bar | 7N NH$_3$ MeOH (50 vol) | 91.7 | 0 | 1.7 | 0 |

Example 25

A reduction reaction was performed was with 75 wt % catalyst with 50 volumes of 7N methanolic ammonia. The reaction was actively maintained at 20° C. overnight. The reaction went to 84.5% product (further conversion to completion would be expected with a sufficiently long stir out time). The result is shown in Table 23. This reaction showed that a reduction in catalyst loading may be compensated for by an increase in temperature.

TABLE 23

| Catalyst Active wt % | Time/ Temp | Pressure | Solvent | Product % by LC | Imine % by LC | SM % LC | Dimer % by LC |
|---|---|---|---|---|---|---|---|
| 75 wt % | 18 h/20° C. | 9 bar | 7N NH$_3$ MeOH (50 vol) | 84.5 | 6 | 5.7 | 0 |

Example 26

Two further reactions were performed with a lower catalyst loading (50% wt active catalyst) with stirring at 30° C. using 50 volumes of 7N and 1N methanolic ammonia. The 7N reaction was heated at 30° C. over the weekend.

TABLE 24

| Catalyst Active wt % | Time/ Temp | Pressure | Solvent | Product % by LC | imine % by LC | SM % LC | Dimer % by LC |
|---|---|---|---|---|---|---|---|
| 50 wt % | 72 h/ 30° C. | 9 bar | 7N NH$_3$ MeOH (50 vol) | 84 | 4 | 1.2 | 4.6 |

The second reaction using 1N methanolic ammonia gave 77% product (4% dimer) after 18 h, however further stirring resulted in erosion of product through reaction with the intermediate imine, resulting in increased levels of dimer. This may be attributable to loss of ammonia at the slightly elevated temperature. The results from the 1N methanolic ammonia reaction are shown in Table 25.

TABLE 25

| Catalyst Active wt % | Time/ Temp | Pressure | Solvent | Product % by LC | imine % by LC | SM % LC | Dimer % by LC |
|---|---|---|---|---|---|---|---|
| 50 wt % | 18 h/ 30° C. | 9 bar | 1N NH$_3$ MeOH (50 vol) | 77 | 7 | 7 | 4.6 |
| 50 wt % | 48 h/ 30° C. | 9 bar | 1N NH$_3$ MeOH (50 vol) | 70 | 5.4 | 1 | 18.8 |

Example 27

All of the nitrile hydrogenation reactions described thus far had used Raney Nickel (50% slurry in water, Acros). The use of alternative catalysts was investigated, starting with Evonik Raney Nickel catalyst MC512, a catalyst specifically developed to minimize the formation of dimeric impurities in nitrile reductions. The Evonik catalyst gave 56% product with 31% starting material remaining (50% wt catalyst in 1N MeOH/NH$_3$, 24 h, 20° C.).

Another reaction was performed using Raney Nickel 3202 supplied from Aldrich; this gave 60% product, 8% starting material and 18% dimer (50% wt catalyst in 1N MeOH/NH$_3$, 48 h, 30° C.).

The current best procedure for the reduction of the nitrile intermediate uses 50 volumes of 7N methanolic ammonia with 50-100 wt % Raney Nickel maintained at 20° C. overnight under 9 bar hydrogen to give complete conversion to product (91.7%, Table 22).

Example 28

High Yield Process

To a Parr hydrogenator was added the 50% wet Raney Nickel catalyst (2 g), 7N methanolic ammonia (50 mL) and 2-(2-(mesitylimino)-9,10-dimethoxy-4-oxo-6,7-dihydro-2H-pyrimido[6,1-a]isoquinolin-3(4H)-yl)acetonitrile (stage 5' intermediate, 1 g, >95% purity by NMR assay). The reaction was warmed to 20° C. and pressurized to 9 bar hydrogen overnight. LC indicated complete consumption of starting material (91.7% product).

The reaction mixture was filtered and washed with methanol (25 mL). The filtrate was concentrated in vacuo. The residue was dissolved in 1M HCl (30 mL) and washed with dichloromethane (DCM, 3×15 mL). The aqueous was then basified with NaHCO$_3$ to pH8 and the solid filtered. The solid was dried over magnesium sulfate to give 700 mg. $^1$H NMR analysis (shown below) indicated the desired amine product with a purity of >95%. The molar yield was 69%. This material was used to prepare RPL554 with a purity >97%.

The new route via the nitrile intermediate (Scheme 1) has the following benefits.

Bromoethylphthalimide (8 equivalents) can be replaced with the much cheaper and more readily available bromoacetonitrile (2.2 equivalents).

The solvent for the alkylation reaction can be changed from the very expensive cyclopentanone (a significant contributor to cost of goods) to acetonitrile.

The long, difficult and low yielding (~40%) work up of the old procedure can be replaced with a more straightforward procedure and the yield of the new alkylation reaction is over 85%.

The new process gives a quicker, cheaper, higher throughput reaction in a much better yield.

The unmasking of the latent amine functionality in the original process required the use of the highly toxic (and genotoxic) hydrazine to remove the phthalimide protecting group (typical yield 85%). The new amine unmasking process involves the reduction of a nitrile group with Raney Nickel to give the amine in a yield of ~70% in similar purity to the product derived from the phthalimide deprotection route.

Substrate conversions in excess of 90% can be readily achieved. High catalyst loading is not necessarily a major concern, as Raney Nickel is cheap, and can be recycled if necessary.

The combined yield of the new alkylation and reduction reactions using the bromoacetonitrile chemistry is currently ~60%, which compares very favourably with the yield of around 40% using the previous phthalimidoethyl alkylation approach previously used for RPL554 manufacture.

Analytical Method

Lc Conditions:

System: Agilent 1100 series liquid chromatograph or equivalent
Column: Acquity BEH Phenyl 4.6×30 mm; 1.7 μm particle size (Ex. Waters #186004644)
Mobile phase A: Water:TFA (100:0.03)
Mobile phase B: Acetonitrile:TFA (100:0.03)
Flow rate: 2.0 ml·min$^{-1}$
Injection volume: 5 μl
Detection: UV detection (Default 254 nm, wavelength project dependent)
Column temp.: 40° C.
Post run: 2.3 mins
Gradient:

| Time (mins) | % A | % B |
|---|---|---|
| 0 | 95 | 5 |
| 5.2 | 5 | 95 |
| 5.7 | 5 | 95 |
| 5.8 | 95 | 5 |
| 6.2 | 95 | 5 |

Mass Spec Conditions:

| | |
|---|---|
| System: | Bruker Esquire 3000 Plus Ion Trap MS |
| Ion Polarity: | Positive |
| Ion Source Type: | ESI |
| Nebuliser: | 50 psi |
| Dry Gas: | 10 l/min |
| Dry Temperature: | 350° C. |
| Target Mass: | 400 m/z |
| Scan Range: | 50 m/z-1000 m/z |

Sample Preparation:

Default preparation is approximately 0.5 mg·ml$^{-1}$ in MeCN:Water (1:1), using sonication to fully dissolve sample.

The invention claimed is:
1. A nitrile compound or a salt thereof, which nitrile compound is a compound of formula (A):

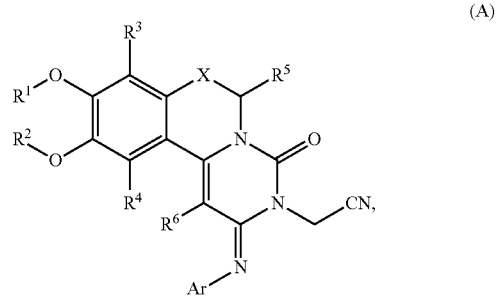

wherein:
$R^1$ and $R^2$ are the same or different and each is independently a C$_1$-C$_6$ alkyl group or a C$_2$-C$_7$ acyl group, or $R^1$ and $R^2$ together form a C$_1$-C$_6$ alkylene group;

R$^3$ and R$^4$ are the same or different and each is independently hydrogen, halogen or a C$_1$-C$_6$ alkyl group;
R$^5$ and R$^6$ are the same or different and each is independently hydrogen, halogen or a C$_1$-C$_6$ alkyl group;
X is CHR$^7$, O or NR$^7$, and R$^7$ is hydrogen or a C$_1$-C$_6$ alkyl group; and
Ar is a C$_6$-C$_{10}$ aryl group substituted with from 0 to 4 substituents, each of which substituents is independently halogen or a C$_1$-C$_6$ alkyl group.

2. A nitrile compound according to claim 1 or a salt thereof, wherein the nitrile compound is a compound of formula (D):

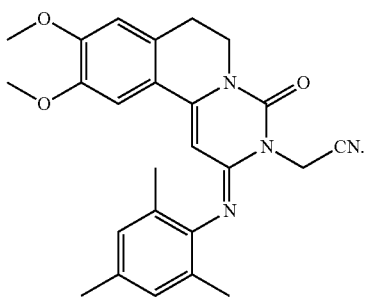

(D)

3. A process for producing a nitrile compound of formula (A) as defined in claim 1, which process comprises reacting a compound of formula (I) with a compound of formula (II):

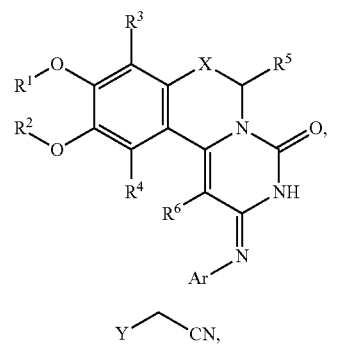

(I)

(II)

wherein
R$^1$ and R$^2$ are the same or different and each is independently a C$_1$-C$_6$ alkyl group or a C$_2$-C$_7$ acyl group, or R$^1$ and R$^2$ together form a C$_1$-C$_6$ alkylene group;
R$^3$ and R$^4$ are the same or different and each is independently hydrogen, halogen or a C$_1$-C$_6$ alkyl group;
R$^5$ and R$^6$ are the same or different and each is independently hydrogen, halogen or a C$_1$-C$_6$ alkyl group;
X is CHR$^7$, O or NR$^7$, and R$^7$ is hydrogen or a C$_1$-C$_6$ alkyl group;
Ar is a C$_6$-C$_{10}$ aryl group substituted with from 0 to 4 substituents, each of which substituents is independently halogen or a C$_1$-C$_6$ alkyl group; and
Y is a leaving group.

4. A process according to claim 3, wherein:
R$^1$ and R$^2$ are methyl;
R$^3$ and R$^4$ are hydrogen;
R$^5$ and R$^6$ are hydrogen;
X is CH$_2$; and
Ar is 2,4,6-trimethylphenyl.

5. A process according to claim 3, wherein Y is a leaving group which is Cl, Br, I, —OC(O)R$^Y$, —OS(O)$_2$R$^Y$ and —S(O)$_2$R$^Y$, where R$^Y$ is hydrogen, a C$_1$-C$_6$ alkyl group, a C$_1$-C$_6$ alkoxy group or a C$_6$-C$_{10}$ aryl group, which alkyl, alkoxy or aryl group is optionally substituted with from 1 to 6 halide groups.

6. A process according to claim 3, wherein the amount of the compound of formula (II) is from 0.5 to 10.0 equivalents of the compound of formula (I).

7. A process according to claim 3, wherein the process comprises reacting the compound of formula (I) and the compound of formula (II) in the presence of a base.

8. A process according to claim 7, wherein the base comprises carbonate, hydrogen carbonate, an alkoxide, a carboxylate or an amine.

9. A process according to claim 7, wherein the amount of the base is from 1.0 to 10.0 equivalents of the compound of formula (I).

10. A process according to claim 3, wherein the process comprises reacting the compound of formula (I) and the compound of formula (II) in the presence of a solvent.

11. A process according to claim 3, wherein the process comprises reacting the compound of formula (I) and the compound of formula (II) for at least 5 hours.

12. A process according to claim 3, wherein the process comprises reacting the compound of formula (I) and the compound of formula (II) at a temperature of from 50 to 100° C.

13. A process for producing a compound of formula (B):

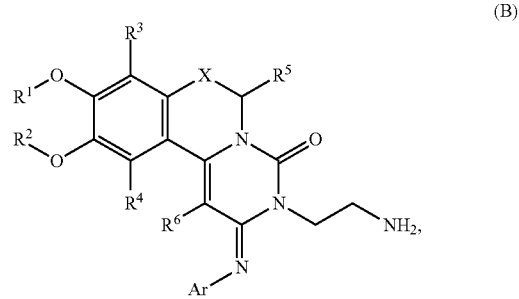

(B)

which process comprises reducing a compound of formula (A) as defined in claim 1.

14. A process according to claim 13, wherein reducing the compound of formula (A) comprises hydrogenating the compound of formula (A) in the presence of nickel, Raney nickel, palladium, palladium black, palladium hydroxide, platinum and platinum dioxide.

15. A process according to claim 13, which process further comprises producing the compound of formula (A) by a process comprising reacting a compound of formula (I) with a compound of formula (II):

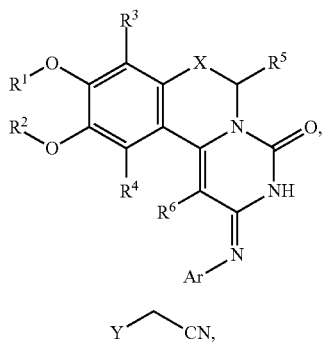

(I)

(II)

wherein
- $R^1$ and $R^2$ are the same or different and each is independently a $C_1$-$C_6$ alkyl group or a $C_2$-$C_7$ acyl group, or $R^1$ and $R^2$ together form a $C_1$-$C_6$ alkylene group,
- $R^3$ and $R^4$ are the same or different and each is independently hydrogen, halogen or a $C_1$-$C_6$ alkyl group;
- $R^5$ and $R^6$ are the same or different and each is independently hydrogen, halogen or a $C_1$-$C_6$ alkyl group;
- X is $CHR^7$, O or $NR^7$, and $R^7$ is hydrogen or a $C_1$-$C_6$ alkyl group, and
- Ar is a $C_6$-$C_{10}$ aryl group substituted with from 0 to 4 substituents, each of which substituents is independently halogen or a $C^1$-$C^6$ alkyl group, and
- Y is a leaving group.

16. A process for producing a compound of formula (C):

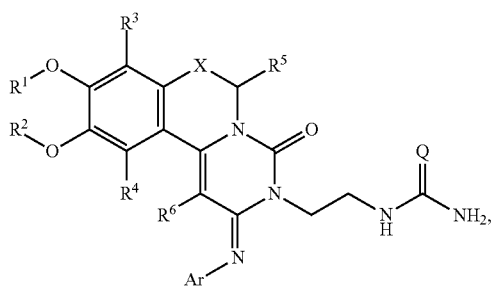

(C)

wherein
- $R^1$ and $R^2$ are the same or different and each is independently a $C_1$-$C_6$ alkyl group or a $C_2$-$C_7$ acyl group, or $R^1$ and $R^2$ together form a $C_1$-$C_6$ alkylene group;
- $R^3$ and $R^4$ are the same or different and each is independently hydrogen, halogen or a $C_1$-$C_6$ alkyl group;
- $R^5$ and $R^6$ are the same or different and each is independently hydrogen, halogen or a $C_1$-$C_6$ alkyl group;
- X is $CHR^7$, O or $NR^7$, and $R^7$ is hydrogen or a $C_1$-$C_6$ alkyl group; and
- Ar is a $C_6$-$C_{10}$ aryl group substituted with from 0 to 4 substituents, each of which substituents is independently halogen or a $C_1$-$C_6$ alkyl group; and
- Q is O, $NR^8$ or $CR^8$ and $R^8$ is hydrogen or a $C_1$-$C_6$ alkyl group, which process comprises:
(i) a process for producing a compound of formula (A)

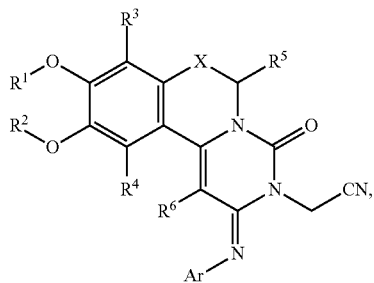

(A)

comprising reacting a compound of formula (I) with a compound of formula (II):

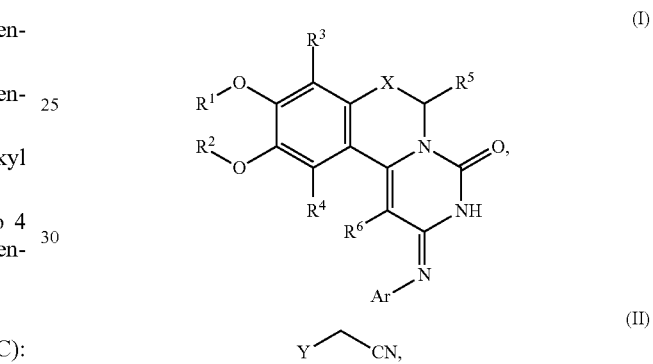

(I)

(II)

wherein
- $R^1$ and $R^2$ are the same or different and each is independently a $C_1$-$C_6$ alkyl group or a $C_2$-$C_7$ acyl group, or $R^1$ and $R^2$ together form a $C_1$-$C_6$ alkylene group;
- $R^3$ and $R^4$ are the same or different and each is independently hydrogen, halogen or a $C_1$-$C_6$ alkyl group;
- $R^5$ and $R^6$ are the same or different and each is independently hydrogen, halogen or a $C_1$-$C_6$ alkyl group;
- X is $CHR^7$, O or $NR^7$, and $R^7$ is hydrogen or a $C_1$-$C_6$ alkyl group; and
- Ar is a $C_6$-$C_{10}$ aryl group substituted with from 0 to 4 substituents, each of which substituents is independently halogen or a $C_1$-$C_6$ alkyl group; and
- Y is a leaving group; and/or (ii) a process for preparing a compound of formula (B) by reducing a compound of formula (A).

17. A process according to claim 16, which process comprises:
(a) preparing a compound of formula (B) by reducing the compound of formula (A); and
(b) further reacting the compound of formula (B) to give a compound of formula (C).

18. A process according to claim 17, wherein step (b) is an ureation reaction.

19. A process according to claim 16, wherein
- $R^1$ and $R^2$ are methyl;
- $R^3$ and $R^4$ are hydrogen;
- $R^5$ and $R^6$ are hydrogen;
- X is $CH_2$;
- Ar is 2,4,6-trimethylphenyl; and
- Q is O.

20. A process according to claim 5, wherein Y is a leaving group which is Br, I, OMs, OTs, ONs, OAc or OTf.

21. A process according to claim 20, wherein Y is a leaving group which is Br.

22. A process according to claim 6, wherein the amount of the compound of formula (II) is from 1.0 to 2.5 equivalents of the compound of formula (I).

23. A process according to claim 8, wherein the base is lithium carbonate, sodium carbonate, potassium carbonate, caesium carbonate, lithium acetate, sodium acetate or potassium acetate.

24. A process according to claim 23, wherein the base is lithium carbonate or sodium acetate.

25. A process according to claim 9, wherein the amount of the base is from 1.5 to 3.0 equivalents of the compound of formula (I).

26. A process according to claim 10, wherein the solvent comprises a polar aprotic solvent.

27. A process according to claim 26, wherein the solvent comprises acetonitrile, tetrahydrofuran or dioxane.

28. A process according to claim 12, wherein the process comprises reacting the compound of formula (I) and the compound of formula (II) in the presence of a solvent at reflux.

29. A process according to claim 14, wherein reducing the compound of formula (A) comprises hydrogenating the compound of formula (A) in the presence of Raney nickel.

30. A process according to claim 18, wherein the ureation reaction is conducted by reacting a compound of formula (B) with a compound $O=C=N^-Z^+$, where $Z^+$ is a metal cation.

31. A process according to claim 30, wherein $Z^+$ is sodium or potassium.

* * * * *